United States Patent [19]

Corish et al.

[11] Patent Number: 5,533,995
[45] Date of Patent: Jul. 9, 1996

[54] PASSIVE TRANSDERMAL DEVICE WITH CONTROLLED DRUG DELIVERY

[75] Inventors: John Corish; Owen I. Corrigan, both of Dublin, Ireland

[73] Assignee: Elan Corporation, plc, Athlone, Ireland

[21] Appl. No.: 244,094

[22] PCT Filed: Nov. 10, 1992

[86] PCT No.: PCT/IE92/00021

§ 371 Date: May 13, 1994

§ 102(e) Date: May 13, 1994

[87] PCT Pub. No.: WO93/09842

PCT Pub. Date: May 27, 1993

[30] Foreign Application Priority Data

Nov. 13, 1991 [IE] Ireland ................................. 3941/91

[51] Int. Cl.$^6$ ................................. A61K 9/22
[52] U.S. Cl. ................... 604/890.1; 604/290; 424/449
[58] Field of Search .................. 604/20, 304, 890.1, 604/891.1, 892.1, 290; 424/449

[56] References Cited

U.S. PATENT DOCUMENTS

| | | | |
|---|---|---|---|
| 3,923,426 | 12/1975 | Theeuwes | 417/48 |
| 4,639,244 | 1/1987 | Rizk et al. | 604/19 |
| 4,722,726 | 2/1988 | Sanderson et al. | 604/20 |
| 4,731,049 | 3/1988 | Parsi | 604/20 |
| 4,942,883 | 7/1990 | Newman | 424/449 |
| 4,943,435 | 7/1990 | Baker et al. | 604/304 |
| 5,041,107 | 8/1991 | Heil, Jr. | 604/892.1 |
| 5,156,591 | 10/1992 | Gross et al. | 604/20 |
| 5,186,805 | 2/1993 | Gross et al. | 204/265 |
| 5,356,632 | 10/1994 | Gross et al. | 604/20 |

FOREIGN PATENT DOCUMENTS

| | | | |
|---|---|---|---|
| 0532451 | 3/1993 | European Pat. Off. | A61N 1/30 |
| 4040911 | 6/1991 | Germany | A61N 1/30 |
| WO9004432 | 5/1990 | WIPO | A61N 1/00 |

*Primary Examiner*—Randall L. Green
*Assistant Examiner*—Mark Bockelman
*Attorney, Agent, or Firm*—Marla J. Church

[57] ABSTRACT

A transdermal device for the controlled administration of a drug to the skin comprises a reservoir (12) for the drug and an electric circuit which includes an electrode system (13, 14) which is operable to actively transport the drug in a controlled manner from the reservoir (12) towards the skin for transport therethrough, the skin not being part of the electric circuit, and the drug passing through an electrode (13) of said electrode system (13, 14) during the active transport to the skin. The electrode (13) is disposed between the reservoir (12) for the drug and an optional transit chamber (15). The electrode (13) can be permeable to the drug or the electrode can function as a gate, being permeable to the drug in the open condition and less permeable to the drug in the closed condition. The operation of the gate can be determined by the composition or the structure of the electrode (13). The device achieves drug delivery rates comparable to those achieved with iontophoretic devices.

41 Claims, 9 Drawing Sheets

PASSIVE TRANSDERMAL DEVICE WITH CONTROLLED DRUG DELIVERY

TECHNICAL FIELD

This invention relates to a transdermal device for the administration of drugs to the skin and, more particularly, to a device for the systemic delivery of drugs by the transdermal route involving uptake of a given drug by the skin.

BACKGROUND ART

The administration of drugs percutaneously or transdermally has a number of advantages and is favoured in the case where drugs are not effectively administered by the oral route but where systemic administration is required. This is especially true for drugs which are subject to a first-pass hepatic metabolism or which are susceptible to deactivation by digestive enzymes.

There are also a number of problems associated with the administration of drugs by the transdermal route, for example, a rate of uptake of drug which is therapeutically effective may not be achievable. The use of penetration enhancers, for example, dimethylsulphoxide, N,N-dimethylformamide and others is employed to promote uptake. However, such penetration enhancers are not always effective or sufficient to achieve adequate percutaneous absorption.

Also the manufacture of stable transdermal devices can be a problem because it may not be possible to find a carrier medium which can maintain the drug in a stable condition until use and from which the drug can be successfully transported to and into the skin following application of the transdermal device at the site of administration.

For some drugs such as glyceryl trinitrate fluctuations in blood level rather than a continuous constant level is required. Thus there is a need for devices or systems capable of periodic or pulsed drug delivery.

For drugs that are not amenable to passive administration by the percutaneous route or for drugs that are effectively percutaneously absorbed as charged molecules, iontophoretic drug delivery is gaining increasing popularity.

However, iontophoretic drug delivery also has a number of problems, not least of which is the trauma caused by burns and pain which may be associated with the use of this type of delivery which involves migration of drug molecules in the skin under the influence of an electric field. Hence conventional iontophoresis as a means of drug delivery may not achieve good patient compliance.

One solution for dealing with the problems associated with iontophoresis is the electrode device of U.S. Pat. No. 4,722,726, one of the stated objects of which is to provide an iontophoretic drug delivery device that inhibits the current carrying capacity of ions in the carrier medium that compete with the active ingredient and lead to progressive diminution of effective drug transfer during the iontophoretic delivery thereof.

U.S. Pat. No. 4,731,049 discloses a cell for electrically controlled transdermal drug delivery by iontophoresis. The drug is bound on an ion exchange resin or medium or an immobilized ligand affinity medium located in the drug reservoir. Drug delivery occurs upon the application of an electrical current of generally small proportions to the reservoir or to an adjacent ion reservoir separated from the drug reservoir by a semi-permeable membrane.

It is an object of the present invention to provide a device and method for the delivery of drugs by the percutaneous route which obviates the trauma in the form of burns and discomfort experienced by the patient and yet achieves an uptake and control of drug by skin which is enhanced when compared to conventional passive delivery.

Investigations carried out by us have shown that by using an electric circuit within a device to actively transport drug from a drug reservoir forming part of said device, but wherein the skin does not form part of the circuitry of the device in contradistinction to an iontophoretic device, one achieves drug delivery rates greater than those achieved with conventional passive delivery.

DISCLOSURE OF INVENTION

Accordingly, the invention provides a transdermal device for the controlled administration of a drug to the skin, which comprises a reservoir for the drug and an electric circuit which includes an electrode system which is operable to actively transport the drug in a controlled manner from said reservoir towards the skin for transport therethrough, the skin not being part of said electric circuit, and the drug passing through an electrode of said electrode system during said active transport to the skin.

In the present Specification the terms drug and active ingredient are used interchangeably.

In one embodiment, the device includes an electrode which is permeable to said drug.

The electrode which is permeable to the drug to be administered can consist of a porous metallic material. Thus the electrode can consist, for example, of a metal gauze or mesh, of a woven metallic material or of a metal laminate. Suitable metals include platinum, silver or a coated or uncoated metal alloy. Other suitable electrodes include carbon or carbon-based electrodes.

The electrode can also be defined by a closed filament of metal or other conducting material defining a ring, a square or other suitable geometric shape.

Alternatively, the electrode which is permeable to the drug being administered can consist of porous carbon sheeting or of a range of polymeric materials, including conducting polymers, with the required conductivity such as those described in the Handbook of Conducting Polymers Vol I and II; T. A. Skotheim, publishers Marcell Dekker Inc. (1986).

The function of said electrode is to spread an appropriate electrical potential.

In a second embodiment, the device according to the invention includes an electrode which functions as a gate, being permeable to said drug in the open condition and less permeable to said drug in the closed condition. The operation of the gate can be determined by the composition of the electrode or, alternatively, by the structure thereof.

In the case where the operation of the gate is determined by the composition of the electrode, the electrode is suitably composed of a polymeric material with the requisite properties.

When the electrode according to said first or second embodiment is a polymeric material, the polymeric material is suitably one that is susceptible to ion doping or, alternatively, is a polymeric material having ion exchange properties. Polymers which are susceptible to ion doping can be of the donor type or the acceptor type. Following the terminology of semiconductor technology the polymers can be described as n-type or p-type, as appropriate. Suitable examples of polymers with ion exchange properties include both anion exchange resins and cation exchange resins as the circumstances require. Suitable resins are marketed by Rohm and Haas company under the Trade Mark Amberlite. Other suitable materials include fluorinated ion exchange polymers such as that sold under the Trade Mark Nation.

The electrode hereinbefore described can span the width of the reservoir, while having any geometric shape or structure herein described. With such an electrode, the surface thereof distal from the reservoir can be placed in contact with the skin in use. With such an arrangement (hereinafter referred to as Arrangement I) the drug passes through the electrode and enters the skin having been actively transported to the skin surface by the electrode system of the device which includes the electrode hereinbefore described and a further electrode disposed elsewhere in the device, so as to complete the electric circuit.

In an alternative embodiment, the electrode is disposed between the reservoir for the drug and a transit chamber therefor (hereinafter referred to as Arrangement II).

The relative sizes of the reservoir and the transit chamber will depend on the particular drug or drugs to be administered. However, in general the transit chamber will be of a lesser volume than the reservoir. The reservoir and transit chamber, if present, together with the electrode disposed therebetween combined will normally have a thickness of less than 5.0 mm, in particular, in the range 0.2–3.0 mm, more especially 1.0–3.0 mm.

Using an arrangement of a reservoir and a transit chamber as hereinbefore described, a measured quantity of drug can be actively transported at selected intervals of time, such as once-a-day, to the transit chamber from whence it enters the skin over a given period of time.

The polarity of the electrodes is set according to the charge on the ion which is to be transported. The current density is suitably in the range 0.2–1.1 mA cm$^{-2}$. However, much larger current densities than those employed in conventional iontophoretic devices can be used. The absolute value being dependent on the thickness of the transit chamber, if such is present. In the case of the device according to the invention it is contemplated that a current density greater than the latter range could be used without causing skin trauma because the skin does not form part of the circuitry.

The device according to the invention allows the use of higher electrical potentials than those employed in conventional iontophoresis.

In an embodiment of the device which allows for periodic or pulsed drug delivery, the polarity of the electrodes and the magnitude of the voltage can be systematically altered.

The reservoir can be formed of a shaped mass of a material in which the drug is distributed or contained for storage.

The transit chamber can either be composed of the same material as the reservoir or of a different material.

Suitably the material of each of the reservoir and the transit chamber is a gel.

Preferred gel materials are formed from gel forming agents selected from plant extracts, gums, synthetic or natural polysaccharides, polypeptides, alginates and synthetic polymers or a mixture thereof.

Especially preferred gel materials are formed from the gel forming agents agar and carrageenan.

Suitable plant extracts include agar, ispaghula, psyllium, cydonia and ceratonia or a mixture thereof.

Examples of suitable gums include guar gum, acacia gum, ghatti gum, karaya gum and tragacanth gum or a mixture thereof.

Suitable synthetic and natural polysaccharides include alkylcelluloses, hydroxyalkylcelluloses, cellulose ethers, cellulose esters, nitrocelluloses, dextrin, agar, carrageenan, pectin, furcellaran and starch or starch derivatives and mixtures thereof. An example of a preferred starch derivative is sodium starch glycolate. Especially preferred polysaccharides include agar and carrageenan as hereinbefore indicated.

Suitable polypeptides include zein, gelatin, collagen and polygeline or a mixture thereof.

Suitable alginates include alginic acid, propylene glycol alginate and sodium alginate or a mixture thereof.

An especially preferred synthetic polymer is a carboxyvinyl polymer sold under the Trade Mark Carbomer.

As used herein the term "agar" is synonymous with "agar-agar".

Other semi-solid type bases include, in particular, media which form liquid crystalline phases such as distilled monoglycerides sold under the Trade Mark MYVEROL.

However, the reservoir and/or the transit chamber, if present, can equally be formed as a shaped mass of any suitable solid or semi-solid medium formed with the aid of a solidifying agent. As used herein, the term solidifying agent embraces hardening, setting, suspending, thickening and like agents.

In the case of the reservoir, the drug or drugs will be uniformly distributed in the solid, semi-solid or liquid medium.

The surface area of the reservoir and the transit chamber, when present, is preferably in the range 1–10 cm$^2$, more especially 2–7 cm$^2$.

The reservoir will suitably contain the drug in an amount of 5–100 mg.

The reservoir can include one or more auxiliary agents selected from an antimicrobial agent or a preserving agent, an antioxidant, a pH controlling agent, a plasticizer, a surfactant, a penetration enhancer, a humectant, a local anaesthetic or a rubefacient.

Preferred antimicrobial/preserving agents include benzalkonium chloride, cetrimide (cetyltrimethylammonium bromide), benzoic acid, benzyl alcohol, Parabens (Trade Mark for the methyl-, ethyl-, propyl- and butyl-esters of parahydroxybenzoic acid) chlorhexidine, chlorobutanol, phenylmercuric acetate, borate and nitrate, potassium sorbate, sodium benzoate, sorbic acid and thiomersal (mercurithiosalicylate) or a mixture thereof.

Preferred antioxidants include sodium metabisulphite, butylated hydroxyanisole and butylated hydroxytoluene or a mixture thereof.

Preferred pH controlling agents include citric acid and sodium citrate.

Preferred plasticizers include diethylphthalate, dibutylphthalate and tributylcitrate or a mixture thereof.

Preferred surfactants include sodium lauryl sulphate, diethylene glycol monostearate, propylene glycol monostearate, polyethylene glycols as sold under the Trade Mark Macrogol, polysorbates and polyvinyl alcohol or a mixture thereof.

Preferred penetration enhancers include dimethylsulphoxide, N,N- dimethylacetamide, N,N-dimethylformamide, 2-pyrrolidone, N-methyl-2-pyrrolidone, 1-dodecylazacyclo-heptan-2-one, fatty acids such as oleic acid and salts thereof and terpenes or a mixture thereof.

A preferred humectant is glycerol.

Preferred local anaesthetics include lidocaine, benzocaine, lignocaine, methocaine, butylaminobenzoate and procaine or a mixture thereof. The device would include a local anaesthetic mainly to suppress irritation at the site of application thereof.

In order to form the reservoir and/or the transit chamber, the respective elements are formed separately by adding the gelling agent or the solidifying agent, as appropriate, to a solvent in an amount that will result in a suitably semi-solid or solid mass. The mixture thereby obtained is mixed and optionally heated depending on the agent used so as to produce a uniform medium.

The solvent used is preferably water. However, the solvent used may also suitably be an alcohol such as ethanol or stearyl alcohol, glycerol, propylene glycol, polyethylene glycol or a silicone or a mixture thereof, including a mixture with water.

In the case of the reservoir, the drug and any auxiliary agents as hereinbefore described are then added and the resulting mixture mixed to uniformity. The shaped mass which forms the reservoir/transit chamber, as appropriate, is formed by moulding, cutting, punching or slicing the solid or semi-solid mixture so as to form discs or layers of the mixture as required in a manner known per se.

The drug reservoir for use in the device according to the invention can also be a liquid contained in a chamber, said chamber having a drug permeable membrane associated therewith for transport of the drug to the skin in use, optionally through a transit chamber, if present.

With the device according to the invention it is possible to administer a drug which is not normally capable of being administered in effective amounts passively by the transdermal route and to control, in the sense of increasing or decreasing, the delivery of drugs that do penetrate the skin passively.

Examples of drugs which can be administered using the transdermal device according to the invention include nicotine, salbutamol and physostigmine and salts thereof.

Preferred drugs for use in the device according to the invention are basic compounds and basic salts and zwitterionic compounds, including peptides.

When the device according to the invention includes a transit chamber, said transit chamber can include a different drug to that contained in the reservoir.

According to a further embodiment of the invention, a number of electrodes can be disposed in said reservoir.

The transdermal device according to the invention can include controlling means operable by a user to selectively transport a drug within and from said reservoir. Furthermore, the transdermal device according to the invention can be programmable.

The device according to the invention can include means for achieving a periodic or pulsed delivery of drug.

The electric circuit will include a power source which will suitably comprise conventional miniature or "light-weight" batteries. For example, conventional sheet batteries and microbatteries may be used.

The transdermal device according to the invention will comprise a housing for the various elements thereof.

Preferably, the reservoir, transit chamber, if present, and at least one electrode define a unit which is detachably mounted in the housing.

When the transdermal device according to the invention is programmable, a programmable controlling member will be located in the housing together with the counter electrode, the power source and other components of the electric circuit. The programmable controlling member will comprise the microelectronics and memory necessary to achieve a predetermined mode and timing of drug transport within the device.

The unit may be engageable with the housing in such a manner so as to select a programme applicable to the active ingredient in the reservoir such that the programme, when activated, brings about controlled transport of active ingredient in said reservoir at selected intervals of time.

The unit can be replaceable as required, such as every day or once-a-week or even twice-daily. For example, in order to achieve the correct diurnal variation required for certain drugs it may be necessary to replace the device twice-daily.

The unit can be adapted to engage with and affix to the housing in any suitable manner, such as by clipping, snap-fit screwing, wedging, bayonet-joint or otherwise securing the respective parts together.

The unit can also be provided with mechanical or electrical contact means adapted to select a programme applicable to the active ingredient contained in the reservoir, which the programmable controlling member identifies as containing the or each active ingredient and which said controlling member thus recognises should be transported according to a prescribed regimen.

Thus the housing and unit can have one or more co-operating electrical contact(s) which on engagement of the respective parts select a given programme.

Preferably, the housing includes means for indicating that the active ingredient is being actively transported and thus delivered at any given time.

The device may also include means for indicating that the power source has failed or weakened.

The electrical circuit can include alarm means to alert a patient when it is time for the active ingredient to be delivered, in particular, in circumstances where the device is not worn continuously.

Such alarm means can comprise a timing circuit which will give a signal such as a bleep which will prompt the user to apply the device to his body.

The housing or the unit preferably includes means for activating the programme when the respective parts are in the engaged position. The means for activating the programme can be an ON/OFF switch. Such a switch can be of the type which is activated to the ON position only when the device is in situ on the body of a patient to be treated. The ON/OFF switch may be activated to the ON position by pressure exerted by an attachment means when affixed to the body of a patient.

The electric circuit suitably includes means for monitoring and indicating the content of the active ingredient in the reservoir. The inclusion of such means would alert a subject undergoing a treatment regimen using the device if the content of active ingredient is not present in an amount effective for a given treatment.

The electric circuit preferably includes overriding means whereby a subject can activate the device to transport and deliver active ingredient at other than a pre-set time up to a predetermined maximum number of such activations.

Preferably, the housing and the unit, when in the engaged position, form a single unit, the exterior surface of which, in use, simulates the face of a time piece and the single unit is attached to or mounted in a strap or bracelet for application of the device to a limb of a body.

More generally, the device according to the invention can be secured to the body in conventional manner such as by adhesive means, including bioadhesive means, straps, bracelets, and like securing means.

The housing suitably includes a liquid crystal display (LCD). The LCD may display current, voltage, timing and other readings as hereinbefore indicated. The unit may include an ammeter and also a voltage adjuster under the control of a control circuit. The latter circuit may also include a galvanostat which keeps the current constant despite varying resistance of the skin.

The device according to the invention is preferably applied to the flexor surface of the forearm, including the wrist, and also the ankle. In general, such sites show the greatest consistency from individual to individual in terms of drug absorption relative to other sites for drug administration because of the amount of tissue at such sites. Blood vessels are found close to the surface of the skin at such sites which facilitates the up-take of drugs into the systemic circulation.

The reservoir and/or the transit chamber, if present, can be housed in a receptacle which is drug impermeable, thereby, ensuring a unidirectional transport of drug towards to the skin.

The invention will be further illustrated by the following description of an embodiment thereof given by way of example only with reference to the accompanying Drawings.

BEST MODE FOR CARRYING OUT THE INVENTION

Figure 1:
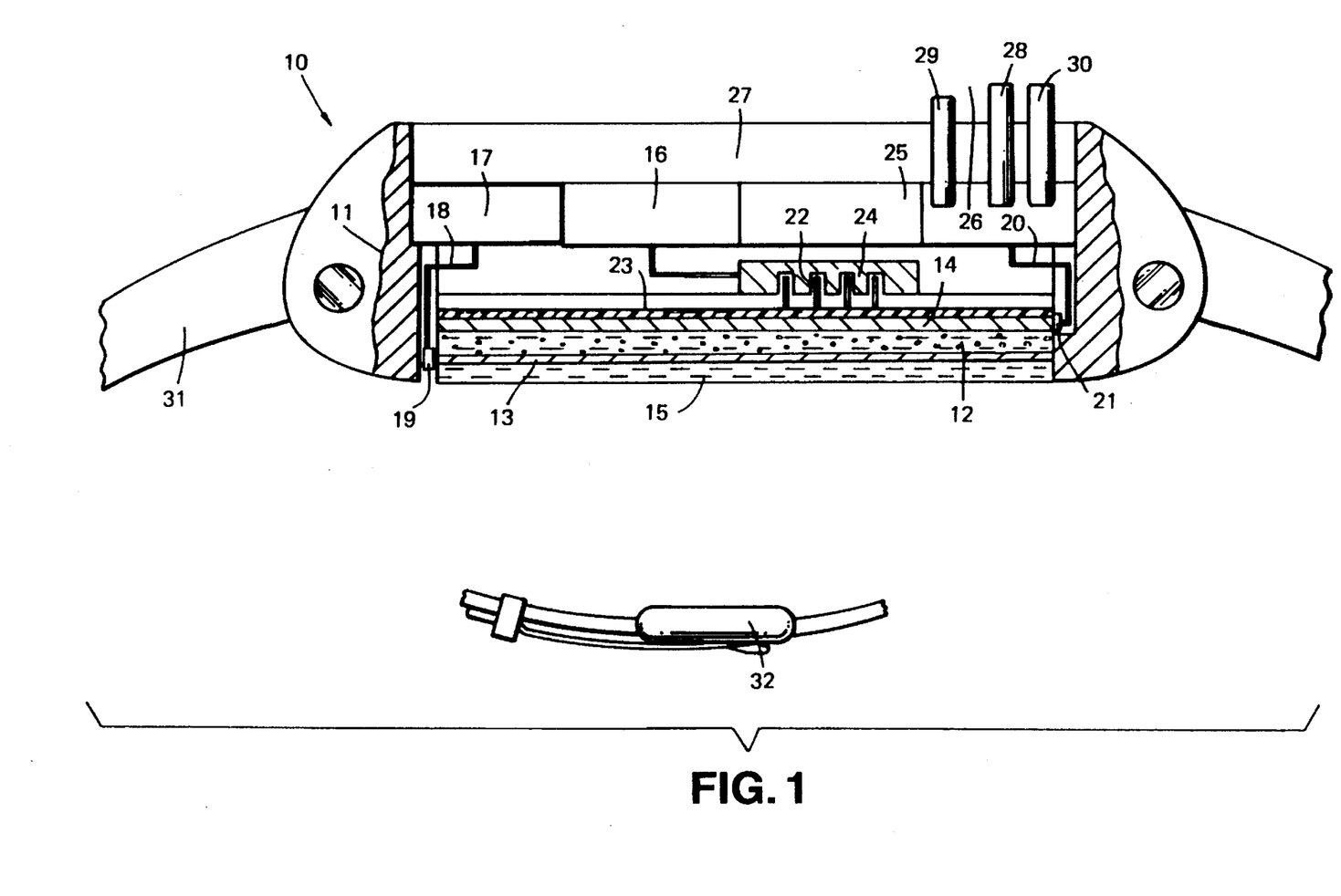
FIG. 1 is a schematic representation of a transdermal device according to the invention (Arrangement II)

Referring to FIG. 1 there is illustrated a transdermal device indicated generally at 10 comprising a housing 11 for a reservoir 12 for a drug uniformly distributed in agar gel and an electric circuit which includes an electrode 13 of platinum mesh gauze (Johnson Matthey 52 mesh Lot No. 625590) which is permeable to said drug and a further electrode 14, the electrode 13 separating the reservoir 12 from a transit chamber 15 also composed of agar gel. The device 10 depicted in FIG. 1 is a device of the type herein referred to as an Arrangement II.

The housing 11 also includes a programmable controlling unit 16 with appropriate circuitry and a power supply 17.

The electrode 13 is connected by a lead 18 through a touch button 19 to the circuitry in the housing 11. The electrode 14 consists of a foil of platinum which is connected to the circuitry in the housing 11 by a lead 20 having an associated touch button 21 and which when the device is activated to transport drug within the reservoir 12 allows the circuit to be completed.

The reservoir 12, the electrode 13 and the transit chamber 15 define a unit which is releaseably attachable to the housing 11 by means of a connector 22 disposed on a surface 23 of an insulating material such as a suitable plastics material. The connector 22 is engageable in a recognition position 24 in the housing 11. The connector 22 on engagement of the aforementioned unit with the housing 11 selects a given programme applicable to the drug contained in the reservoir 12 and said programme when activated brings about the desired transport of the drug to the transit chamber 15 and hence by passive diffusion thereafter to the skin.

The programmable controlling unit 16 includes an ammeter 25, a galvanostat 26 and an LCD 27 with appropriate switching arrangements which can display current, voltage and time and a time keeping component with provision for an audible alarm which alerts a subject when it is time for the drug to be delivered, if the device is not worn continuously. The unit 16 also includes an ON/OFF button 28 for activating the program when the unit comprising the reservoir 12, and the housing 11 are in the engaged position and an override button 29 whereby a patient can activate the device to transport the drug at other than a pre-set time up to a predetermined maximum number of such activations as hereinbefore described.

An LED (light emitting diode) 30 is also provided in the unit 16 to indicate satisfactory operation of the device, for example so as to indicate that the drug is being actively transported. The LED 30 also indicates if the power supply 17 has failed or weakened and will give an indication of the content of the drug in the assembled device.

The device 10 is attached to the site of application by means of a strap 31 having at the free ends thereof the cooperating elements of a conventional clasp 32.

Figure 2:
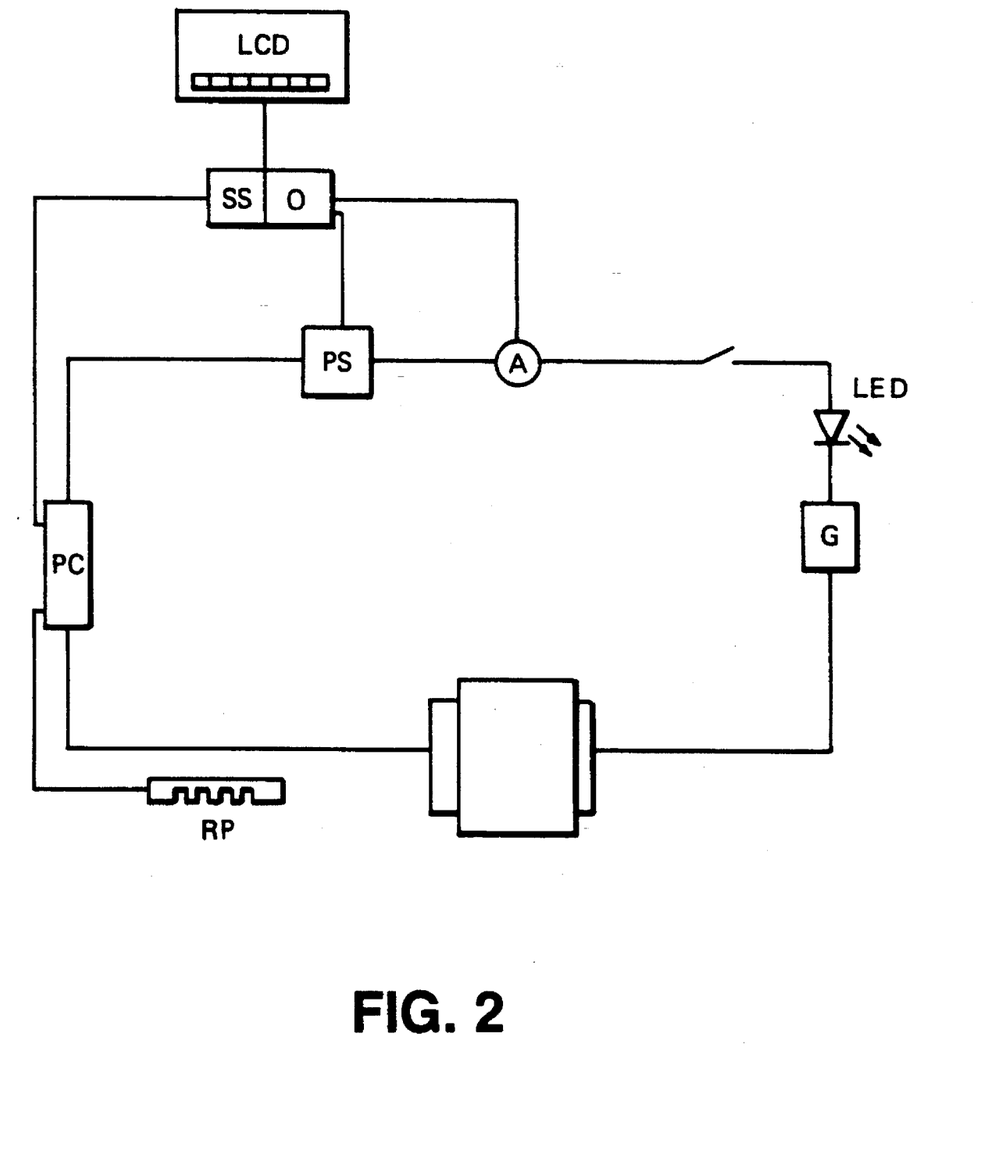
FIG. 2 is a circuit diagram of the circuit employed in the device depicted in FIG. 1.

The main components of the circuit employed in the device 10 are depicted in the circuit diagram corresponding to FIG. 2. Said components are as follows:

PC—a programmable controlling circuit, including an audible alarm means;

PS—a power supply;

A—an ammeter;

G—a galvanostat;

SS—a selector switch;

O—an override switch;

LCD—a liquid crystal display for current, voltage, time, etc. as selected; and

LED—a visible signal of delivery of drug, failure or weakening of power supply, or content of drug in the device 10.

RP—a recognition position.

Most of the foregoing features can be incorporated into an appropriate microchip.

In Vitro Studies—Arrangement II.

A series of in vitro experiments were carded out to assess the transdermal device according to the invention of the type herein referred to as an Arrangement II. In these experiments an artificial membrane of Visking (Visking is a Trade Mark) and human stratum corneum were used as the barriers to diffusion into glass, custom built diffusion cells based on a commercially available Franz cell (Franz, T. J., (1975); J. Invest. Dermatol. 64, 190). An assembly consisting of a reservoir, transit chamber, electrodes, galvanostat and ammeter of the type used in the transdermal device depicted in FIG. 1 and a voltmeter was placed on top of the cell and secured in place by means of a Teflon (Teflon is a Trade Mark) holder.

For the experiments with Visking the solution used in the receptor compartment of the cell was distilled water, whereas for the experiments using human stratum corneum a phosphate buffer at pH 7.4 was used in the receptor compartment. The phosphate buffer solution of pH 7.4 used in the latter experiments was prepared using disodium hydrogen orthophosphate (BDH) 14.7 g/l and sodium dihydrogen phosphate (Riedel-deHaen) 2.66 g/l in distilled water. The receptor solution was stirred throughout the experiment by a star-headed magnet to provide control of the cell hydrodynamics.

The cell was immersed in a water bath, the temperature of which was kept constant at 37° C. to mimic body temperature. Samples of receptor solution were withdrawn through the side arm or sample port of the cell at regular intervals during the course of the experiments and replaced by fresh receptor solution in conventional manner.

The Visking membrane was prepared from 4 cm length sections of Visking tubing 18/32 which were boiled in distilled water before use to free the membrane of any impurities.

Human stratum corneum membrane was prepared in accordance with the method of Kligman, A. M. and Christophers, E. ((1963) Archives Dermatology 88, 702–705). The stratum corneum and the epidermis were separated from the other skin layers from a section of full thickness abdominal skin and the excess subcutaneous fat removed. The remainder of the tissue was immersed in distilled water at 60° C. for 2 min. The usual trypsinisation step to remove the epidermis was omitted. This was considered to be unnecessary as it is known that the stratum corneum is the rate limiting barrier to diffusion of drugs through the skin. The stratum corneum was then stretched onto a wire mesh dermal side down and dried overnight in a desiccator at 25% relative humidity. When dry, it was sealed in a plastics sachet and stored in a fridge until needed.

Preparation of Discs.

Discs of gel No. (1) (Oxoid Ltd. Lot No. 238 14790) were prepared by adding 4% of the solid to distilled water (20 ml) and the resultant mixture was heated slowly. When hot, the viscous solution was poured into a standard size petri dish and allowed to set. Circular discs 1.84 cm. in diameter were cut out and used as the transit chamber in the assembly. A range of discs ranging in thickness from 0.10–0.45 cm were studied.

The drug loaded discs to serve as the reservoir in the assembly were also made of No. (1) gel in which the drug was dissolved. The drug loaded discs were prepared in the same manner as for the discs to serve as the transit chamber with the addition of the requisite amount of drug prior to the heating step. The drugs used in the evaluation of the device were nicotine (vacuum distilled, The Nicobrand Company, Coleraine, County Derry, Northern Ireland.) and salbutamol sulphate B. P. Circular discs, with a cross-sectional area of 2.67 $cm^2$ and a volume of 1.81 $cm^3$ were cut as required. For both salbutamol and nicotine the drug dissolved in water with a little stirring.

Analytical Methods

Salbutamol was detected in the samples withdrawn from the diffusion cell by high performance liquid chromatography (HPLC).

HPLC samples were injected onto a μ Bondapak $C_{18}$ Radical-Pak (Bondapak and Radical-Pak are Trade Marks) reversed column using a Waters 712 WISP (WISP is a Trade Mark) auto-injector. The method of detection employed was UV spectroscopy using a Waters model 455-LCUV spectrophotometer. The mobile phase consisted of acetonitrile (Lab Scan) (92:8) containing 12 g/l $NaH_2PO_4$. The flow rate was set at 2 ml/min. The detection wavelength was set at 276 nm. The injection volume of the sample under analysis was 20 μl. An external standard method was used by means of a Waters 740 Data Module integrator to calculate the concentration of salbutamol. Using this method a sharp peak was observed at a retention time of 6 min. The system was programmed to recalibrate the standard after every 5 samples in order to optimise the accuracy of the analysis.

Determination of nicotine was achieved by UV spectroscopy using a PYE Unicam SP8200 UV/VIS Spectrophotometer with the detection wavelength set at 260 nm.

Control assemblies comprised: a) an assembly consisting of a reservoir (single gel system); b) an assembly consisting of a reservoir superimposed on a transit chamber (double gel system); and c) an assembly as for b) but with a platinum mesh disposed between the reservoir and the transit chamber.

Permeation Studies Across Membranes.

Release of both salbutamol and nicotine from control b) showed a release profile characteristic of a passive system. The lag-time for the delivery through control b) was greater than the value obtained from control a), indicating retarded transport when a transit chamber is present.

The extent to which the transit chamber acts by retarding the delivery of drug can be explained in terms of gel thickness in that chamber. Decreasing the thickness of the gel results in an increased rate of drug penetration through the Visking membrane. Thus, reducing the thickness of the transit chamber enhances the initial rate of drug transport.

As might be expected greater quantities of drug were released from gels that contained higher initial concentrations. Increasing the concentration of drug in the reservoir was also seen to reduce the lag-time.

Incorporation of the platinum gauze (control c)) between the two gels constituting the double gel system introduces a new barrier to drug diffusion. The degree to which the platinum acted as a barrier to drug diffusion depended on the pore size of the mesh itself. The greater the void surface area on the gauze the faster the rate of drug penetration. Introduction of a silver gauze barrier between the two gels also served as a barrier to drug permeation and since the degree of void area for drug penetration was less than that in the platinum gauze membrane, the rate of drug release was hindered to a greater extent.

Device According to the Invention.

Application of a potential difference across the reservoir between the gauze and the electrode applied to the side furthest away from the membrane barrier results in an increase in the rate of penetration of drug through the double gel system. The ensuing electric current results in the movement of charged ions in the drug loaded gel. The basis for this electrolytic movement is provided by Faraday's laws of electrolysis. In the device according to the invention the drug ions are carried through the reservoir from the solid platinum electrode to the platinum gauze electrode. This results in a build up of drug concentration at the interface between the gels. However, due to the porous nature of the gauze membrane, ions gathering at the surface of the electrode may permeate into the second gel (transit chamber) which is initially unloaded, resulting in enhanced movement of drug through the gauze barrier and into the unloaded gel. This provides a means whereby the concentration of drug in the unloaded gel can be controlled and maintained. The actual diffusion of the drug across the Visking barrier is controlled and depends on the concentration that has been built up in the originally unloaded gel in the transit chamber.

The overall rate of delivery ($R_{total}$) of drug from the assembly can be described by the combination of electrically assisted ($R_{elec}$) and passive transport ($R_p$) as $$R_{total} = R_p + R_{elec}$$

It should be emphasised here that the transport through the membrane in the next phase of delivery takes place by diffusion and is not assisted by current as in the case of conventional iontophoretic systems where the membrane (i.e. skin) forms part of the electric circuit.

Figure 3:
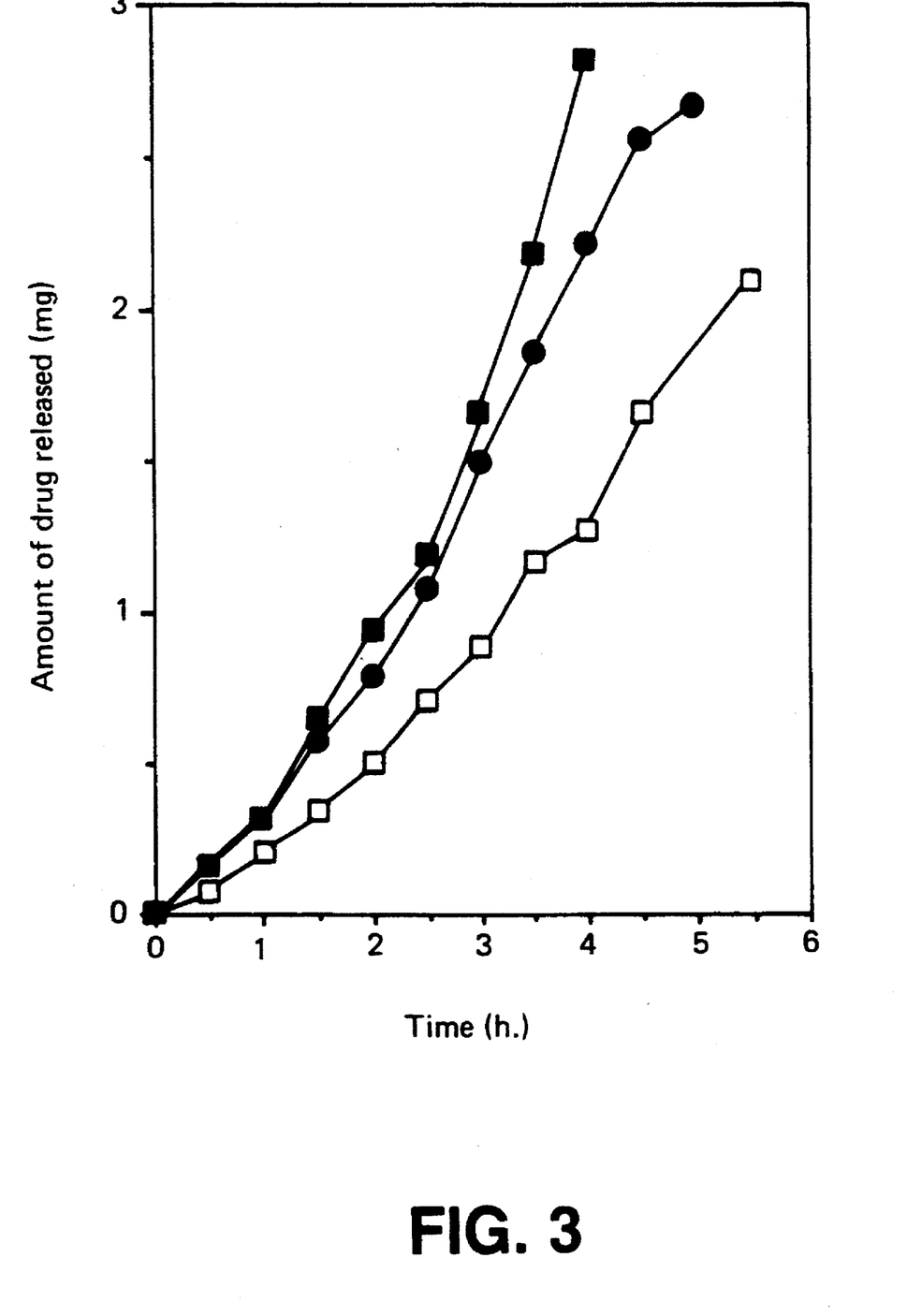
FIG. 3 is a graphic representation of nicotine release profile (mg) versus time (h.) for a device according to the invention relative to controls as hereinafter described.

By comparison with both control b) and control c), the enhancement in drug penetration is clearly evident. Release rates for the three systems are shown to be of the order, platinum barrier system < double gel system < device according to the invention as shown in FIG. 3 which is a comparison of release profiles in the receptor compartment of the diffusion cell obtained from control b) (—●—), control c) (—□—) and the device according to the invention (—■—) using a current of 0.5 mA.

Figure 4:
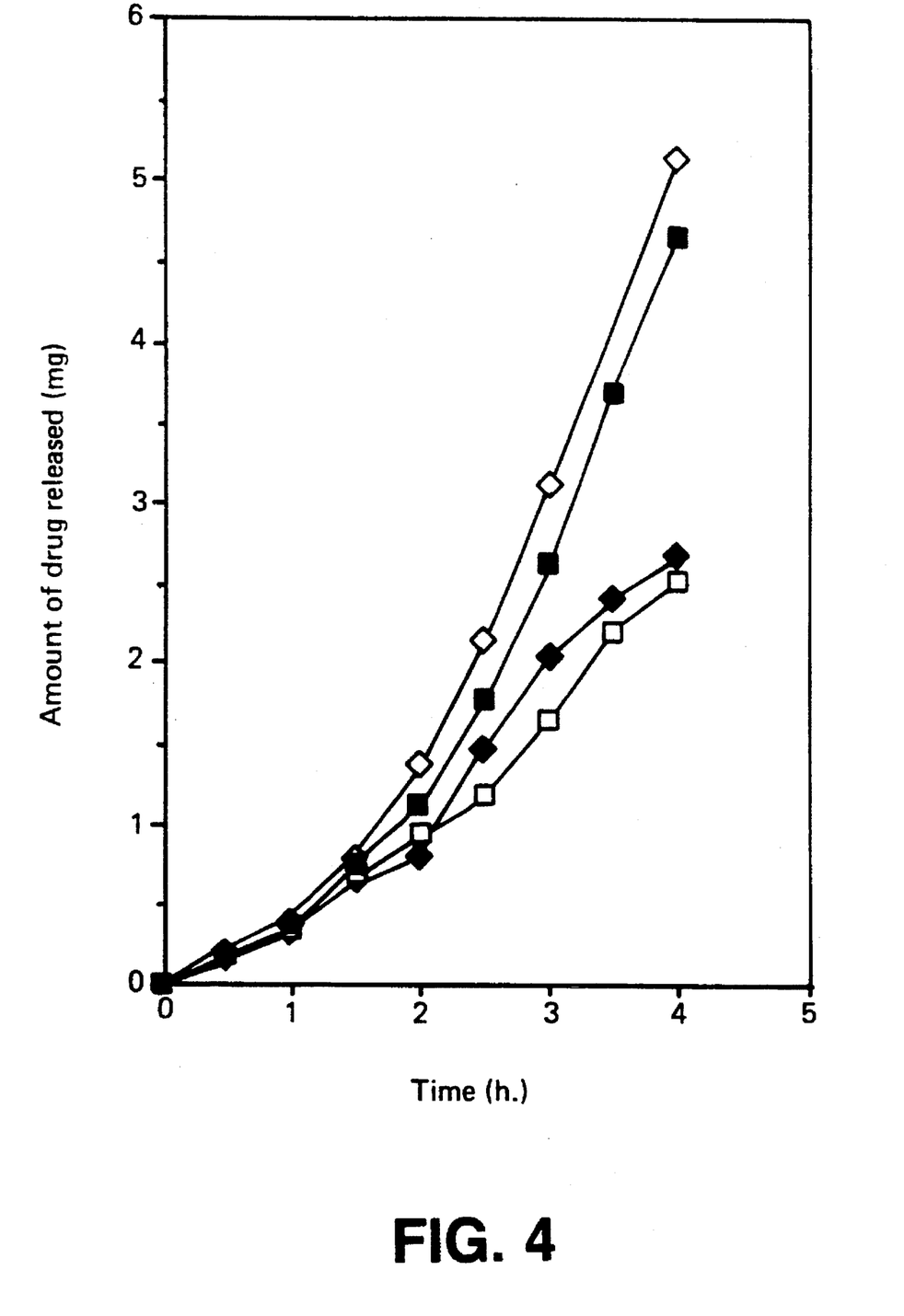
FIG. 4 is a graphic representation of the effect of the current density through a device according to the invention on the quantity of nicotine released (mg) as a function of time (h) as hereinafter described.

The effect of applying a range of currents 0.5–3.0 mA to the device according to the invention, is shown in FIG. 4. As the current is increased the rate of drug transport into the receptor compartment of the diffusion cell also increases and as is the case for single gel iontophoretic systems the release profiles tend to become linear with time. In FIG. 4, curve —□— represents 0.5 mA, curve —♦— represents 1.0 mA, curve —■— represents 2.0 mA and curve —◇— represents 3.0 mA.

Permeation Studies Across Excised Human Stratum Corneum.

Figure 5:
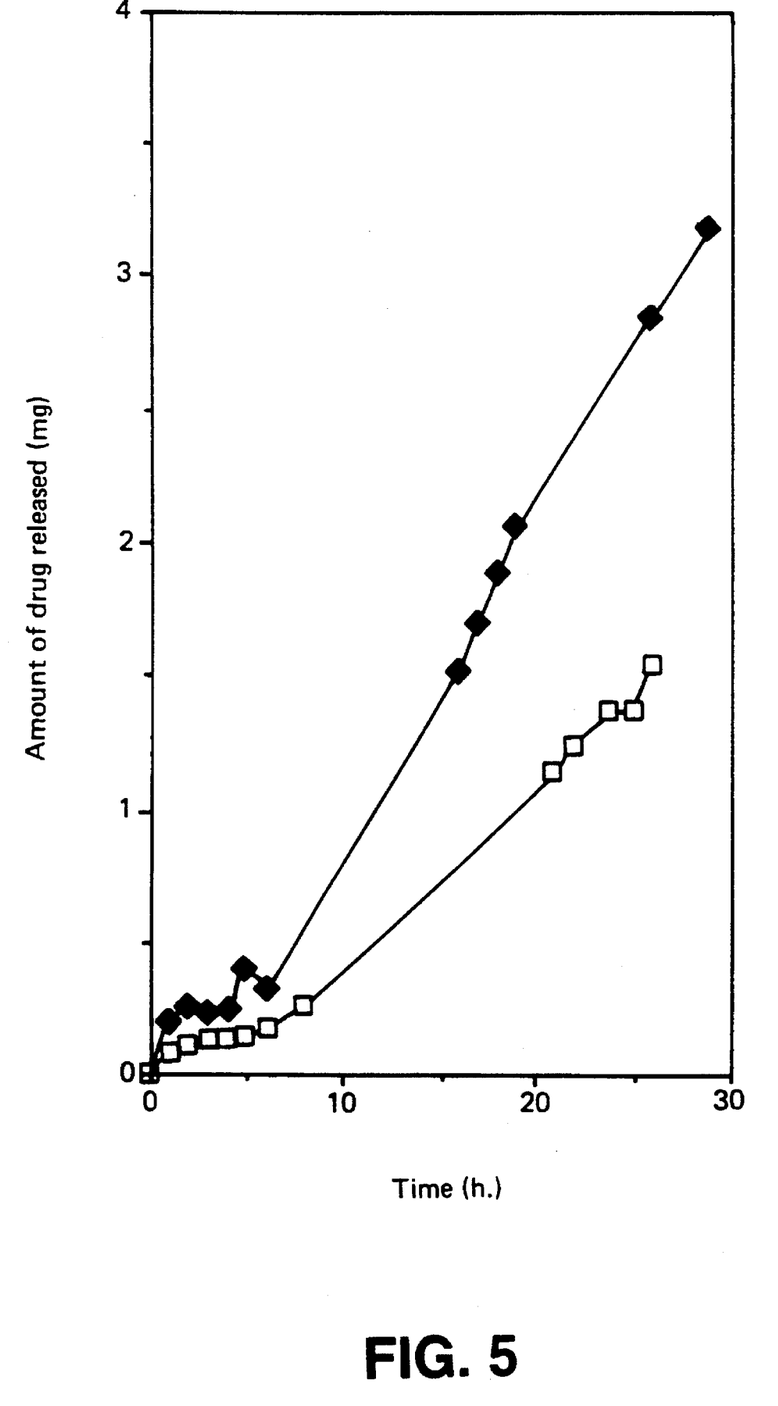
FIG. 5 is a graphic representation of the quantity of drug released (mg) versus time (h.) for 20 mg nicotine-containing discs across human stratum corneum in a device according to the invention relative to a control.

Preliminary investigations across excised human stratum corneum have illustrated similar trends in drug penetration from the device according to the invention to those observed using Visking ie., the same order of drug permeation is observed for each of the three double gel systems namely controls b) and c) and the device according to the invention. The degree of permeability using a 20 mg nicotine patch (11.04 mg/ml), unloaded gel thickness of 2.2 mm for the double gel system, gives quite a slow release of nicotine (FIG. 5). Application of an electrical potential resulting in a current of 0.5 mA flowing through the reservoir gives an approximate 2 fold enhancement in drug penetration. In FIG. 5, curve —□— represents control b) and curve —♦— represents the device according to the invention. The effect of passing greater currents through the drug loaded gels needs to be investigated as studies to date have been confined to the use of a 0.5 mA current.

In Vitro Studies—Arrangement I.

A further series of in vitro experiments were carried out using as biological membranes Sha-Sha mouse skin and whole thickness human skin in conjunction with a device according to the invention without a transit chamber and herein referred to as Arrangement I. The conditions were generally as set out for the in vitro studies carried out on Arrangement II, except as hereinafter described. Thus, in these experiments a carbon-based porous electrode (3M Company) was used. The drug employed was physostigmine either as the hemisulphate or salicylate.

Experiment a).

Drug: physostigmine hemisulphate.

Drug loading: 15.3 mg (=7.84 mg/ml).

Vehicle: 4% agar/water.

Surface area: 2.37 cm².

Receptor solution: isotonic phosphate buffer, pH 7.4.

Membrane: Sha-Sha mouse skin.

Figure 6:
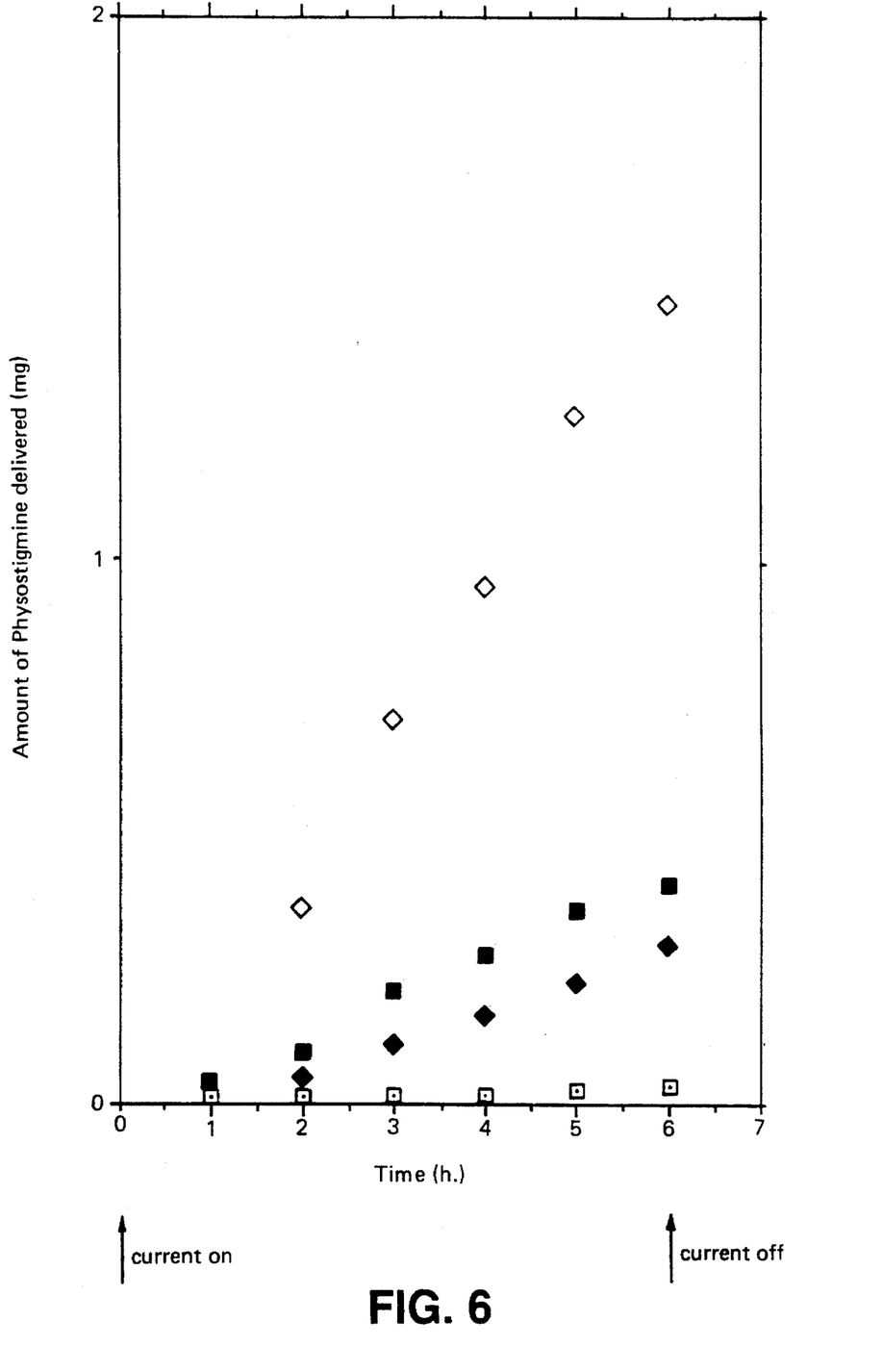
FIG. 6 is a graphic representation of the delivery of physostigmine hemisulphate (mg) across Sha-Sha mouse skin in an Arrangement I-type device according to the invention using different currents versus time (h) relative to passive delivery.

The results are depicted in FIG. 6.

In FIG. 6 curve ▫ represents conventional passive delivery (0.00 mA) while the remaining curves represent delivery from Arrangement I. Curve ♦ represents a current of 0.5 mA, curve ■ represents a current of 1.0 mA and ◇ represents a current of 2.0 mA. A greater than tenfold enhancement in transport is evident with Arrangement I.

Experiment b).

Drug: physostigmine salicylate.

Drug loading: 19.5 mg (=10 mg/ml).

Vehicle: 4% agar/water.

Surface area: 2.37 cm².

Receptor solution: isotonic phosphate buffer, pH 7.4.

Membrane: Sha-Sha mouse skin.

Figure 7:
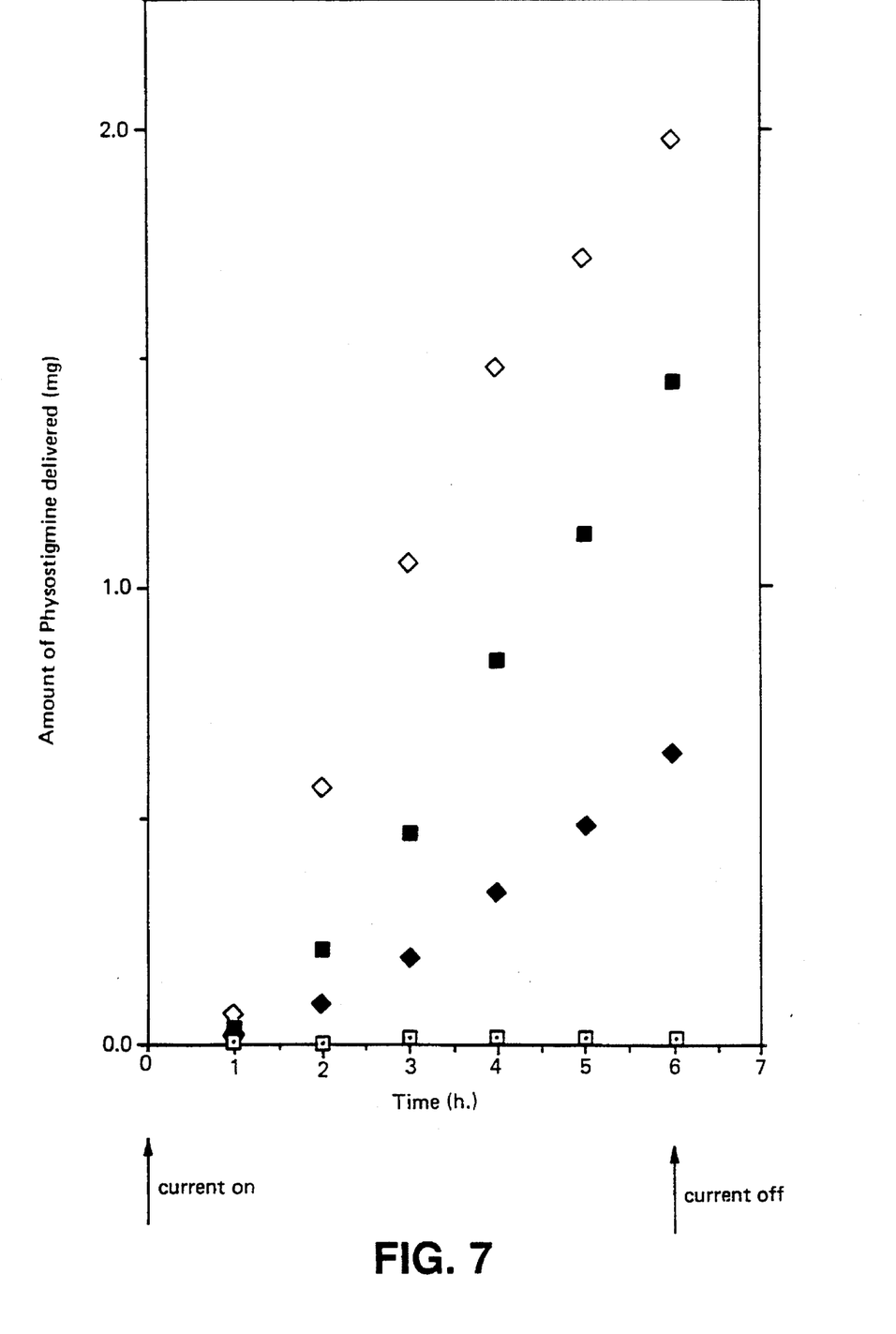
FIG. 7 is a graphic representation of the delivery of physostigmine salicylate (mg) across Sha-Sha mouse skin in an Arrangement I-type device according to the invention using different currents versus time (h) relative to passive delivery.

The results are depicted in FIG. 7.

In FIG. 7 curve ▫ represents conventional passive delivery (0.00 mA) while the remaining curves represent delivery from Arrangement I. Curve ♦ represents a current of 0.5 mA, curve ■ represents a current of 1.0 mA and ◇ represents a current of 2.0 mA. It will be observed from FIG. 7 that an even greater enhancement in transport is evident when the salt form of the drug is changed to the salicylate.

Experiment c).
Drug: physostigmine salicylate.
Drug loading: 30 mg (=10 mg/ml).
Vehicle: 4% agar/water.
Surface area: 7.00 cm$^2$.
Receptor solution: isotonic phosphate buffer, pH 7.4.
Membrane: Sha-Sha mouse skin.
The results are depicted in FIG. 8.

Figure 8:
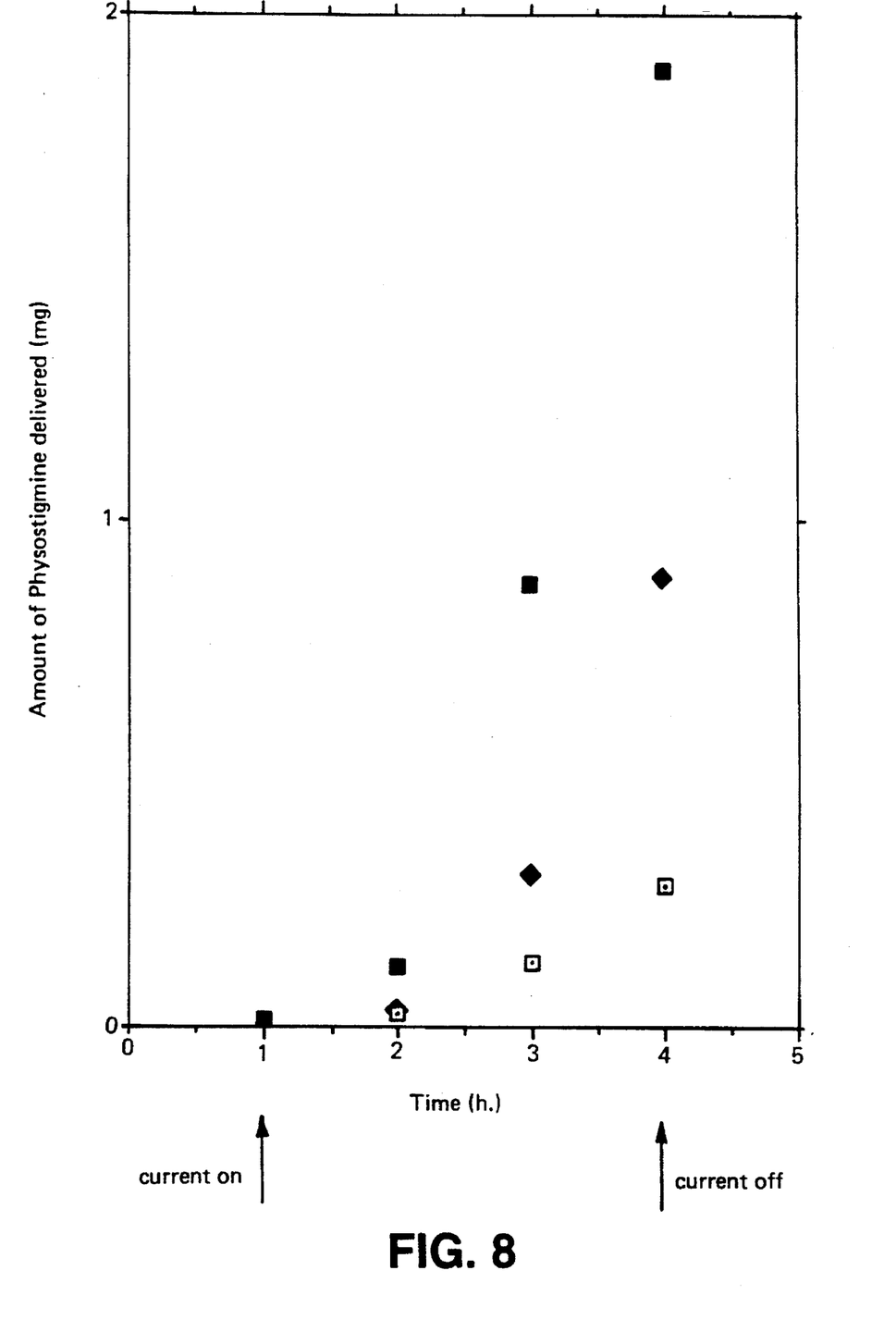
FIG. 8 is a graphic representation of the delivery of physostigmine salicylate (mg) across Sha-Sha mouse skin in an Arrangement I-type device according to the invention using different currents versus time (h) relative to passive delivery, using a different drug loading and surface area relative to that used in relation to FIG. 7.

In FIG. 8 curve ☐ represents a current of 1.475 mA, curve ♦ represents a current of 2.950 mA and ■ represents a current of 4.525 mA. A further relative enhancement in transport is evident under the conditions used in Experiment c) relative to Experiment b).

Experiment d).
Drug: physostigmine salicylate.
Drug loading: 19.5 mg (=10 mg/ml).
Vehicle: 4% agar/water.
Surface area: 2.37 cm$^2$.
Receptor solution: isotonic phosphate buffer, pH 7.4.
Membrane: Whole thickness human cadaver skin.
The results are depicted in FIG. 9.

Figure 9:
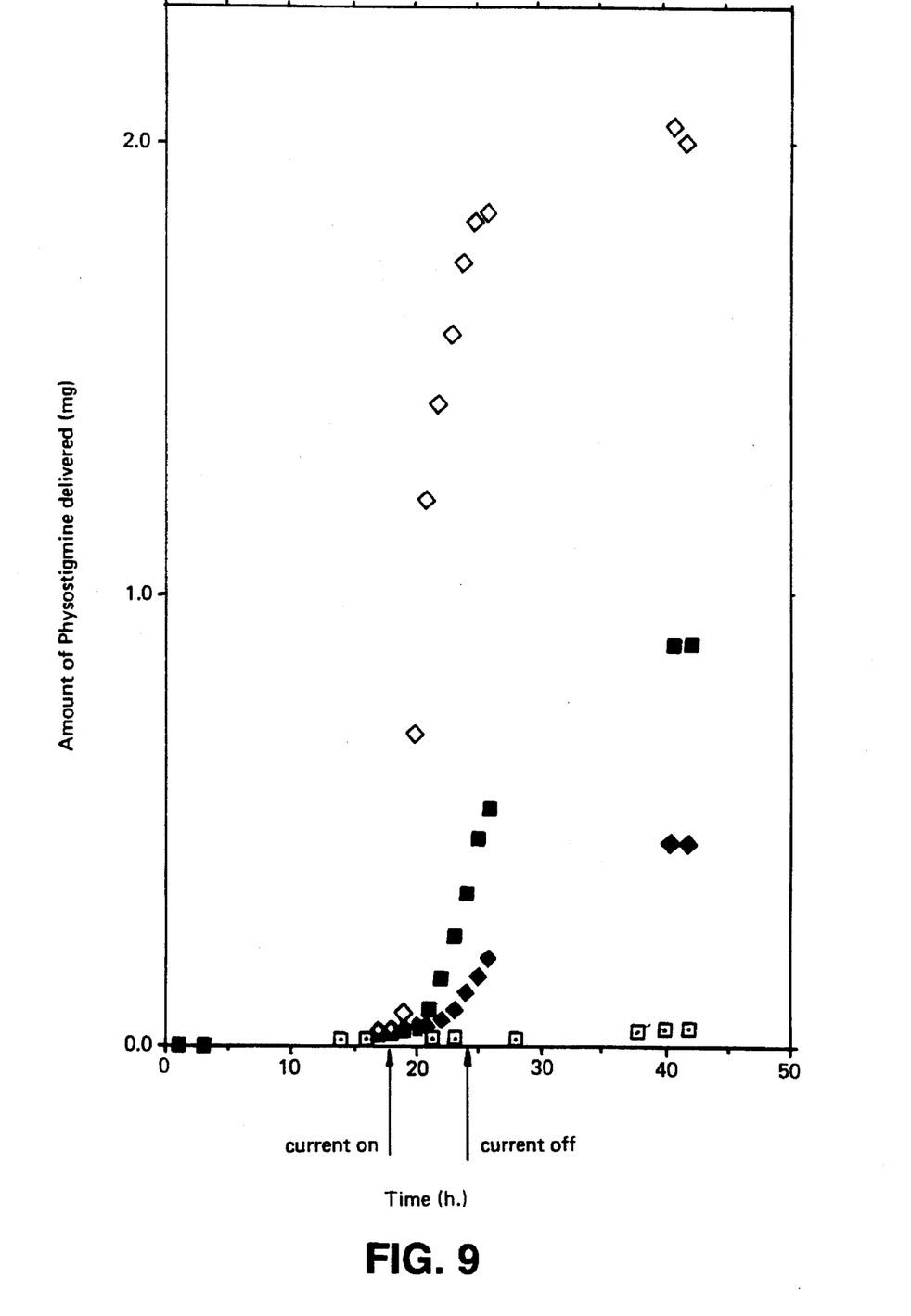
FIG. 9 is a graphic representation of the delivery of physostigmine salicylate (mg) across whole thickness human cadaver skin in an Arrangement I-type device according to the invention using different currents versus time (h) relative to passive delivery.

FIG. 9 shows enhanced delivery of physostigmine from Arrangement I when compared with conventional passive transport (curve ☐ (0.00 mA)). In FIG. 9 curve ♦ represents a current of 0.5 mA, curve ■ represents a current of 1.0 mA and ◊ represents a current of 2.0 mA.

The experiment shows that Arrangement I was also effective when the Sha-Sha mouse skin was replaced by whole thickness human skin.

This invention is not limited to the embodiments described above which may be modified and/or varied without departing from the scope of the invention.

We claim:

1. A transdermal device for the controlled administration of a drug to the skin, which comprises a reservoir for the drug, an electric circuit comprising an electrode system of at least two electrodes in which at least one of the electrodes is permeable to the drug, which electrode system has means for electrolytically transporting the drug in a controlled manner within the device by a potential difference applied to the electrodes, the drug passing through the at least one drug permeable electrode of the electrode system, wherein the electrodes are disposed internally of the device such that the skin does not form a part of the electric circuit, means for securing the device in contact with the external skin of a patient, the drug being actively transported from the reservoir in the direction of the skin for transport therethrough, by energising the electrodes.

2. A transdermal device according to claim 1, wherein the drug is one which is not normally capable of being administered passively by the transdermal route.

3. A transdermal device according to claim 1, wherein the at least one drug permeable electrode comprises a porous metallic material.

4. A transdermal device according to claim 3, wherein the at least one drug permeable electrode comprises a metal gauze.

5. A transdermal device according to claim 3, wherein the at least one drug permeable electrode comprises a woven metallic material.

6. A transdermal device according to claim 3, wherein the at least one drug permeable electrode comprises a metal laminate.

7. A transdermal device according to claim 3, wherein the metal is selected from the group consisting of platinum, silver, a coated metal alloy and an uncoated metal alloy.

8. A transdermal device according to claim 1, wherein the at least one drug permeable electrode comprises carbon sheeting.

9. A transdermal device according to claim 1, wherein the at least one drug permeable electrode functions as a gate, being permeable to the drug in the open condition and less permeable to the drug in the closed condition.

10. A transdermal device according to claim 9, wherein the operation of the gate is provided by the at least one drug permeable electrode being constructed of an ion exchange material.

11. A transdermal device according to claim 9, wherein the operation of the gate is provided by the at least one drug permeable electrode formed of a material of variable pore sizes.

12. A transdermal device according to claim 1, wherein the at least one drug permeable electrode electrode which comprises a polymeric material.

13. A transdermal device according to claim 12, wherein the polymeric material is susceptible to ion doping.

14. A transdermal device according to claim 12, wherein the polymeric material has ion exchange properties.

15. A transdermal device according to claim 1, wherein the at least one drug permeable electrode electrode spans the width of the reservoir.

16. A transdermal device according to claim 1, wherein the at least one drug permeable electrode electrode spans the width of the reservoir and wherein the surface of said at least one drug permeable the electrode distal from the reservoir is placed in contact with the skin in use.

17. A transdermal device according to claim 1, further comprising a transit chamber adapted for contact with the skin, wherein the said at least one drug permeable electrode is disposed between the reservoir for the drug and the transit chamber therefor.

18. A transdermal device for the controlled administration of a drug to the skin, which comprises a reservoir formed of a shaped mass of a material in which the drug is distributed for storage, a transit chamber adapted for contact with the skin, and an electric circuit comprising an electrode system of at least two electrodes, which electrode system is operable to actively transport the drug electrolytically in a controlled manner within the device, the drug passing through an electrode of the electrode system, which electrode is permeable to the drug and is disposed between the reservoir for the drug and the transit chamber therefor, the electrodes being disposed internally of the device such that the skin does not form part of the electric circuit and such that the drug is electrolytically transported from the reservoir in the direction of the skin for transport therethrough, by energising the electrodes.

19. A transdermal device according to claim 18, wherein the transit chamber is composed of the same material as the reservoir (12).

20. A transdermal device according to claim 18, wherein the transit chamber is composed of a material which is different to that comprising the reservoir.

21. A transdermal device according to claim 18, wherein the material of each of the reservoir and the transit chamber is a gel.

22. A transdermal device according to claim 21, wherein the gel material is formed from a gel forming agent selected from the group consisting of plant extracts, gums, synthetic or natural polysaccharides, polypeptides, alginates, synthetic polymers and mixtures thereof.

23. A transdermal device according to claim 21, wherein the gel forming agent selected from the group consisting of agar and carrageenan.

24. A transdermal device according to claim 18, wherein the transit chamber includes a different drug to that contained in the reservoir.

25. A transdermal device according to claim 18, wherein the drug is one which is not normally capable of being administered passively by the transdermal route.

26. A transdermal device according to claim 18, wherein the drug is salbutamol.

27. A transdermal device according to claim 18, wherein the drug is nicotine.

28. A transdermal device according to claim 18, wherein a plurality of electrodes permeable to the drug are disposed in the reservoir.

29. A transdermal device according to claim 18, wherein the device includes controlling means operable by a user to selectively transport the drug within and from the reservoir.

30. A transdermal device according to claim 18, further comprising programmable means for controlling the selective transport of the drug within and from the reservoir.

31. A transdermal device according to claim 18, further comprising means for achieving a periodic or pulsed delivery of drug.

32. A transdermal device according to claim 18, further comprising housing means, wherein the reservoir, transit chamber and at least one electrode define a unit which is detachably mounted in the housing means.

33. A transdermal device according to claim 1, wherein the drug is salbutamol.

34. A transdermal device according to claim 1, wherein the drug is nicotine.

35. A transdermal device according to claim 2, wherein a plurality of electrodes permeable to the drug are disposed in the reservoir.

36. A transdermal device according to claim 1, wherein the device includes controlling means operable by a user to selectively transport the drug within and from the reservoir.

37. A transdermal device according to claim 1, further comprising programmable means for controlling the selective transport of the drug within and from the reservoir.

38. A transdermal device according to claim 1, further composing means for achieving a periodic or pulsed delivery of drug.

39. A transdermal device according to claim 1, further comprising housing means, wherein the reservoir and at least one electrode define a unit which is detachably mounted in the housing means.

40. A method for the controlled passive transdermal delivery of at least one drug to a subject, comprising the steps of:
  (a) attaching a transdermal device to the skin of the subject, wherein the transdermal device comprises:
    i) the at least one drug;
    ii) a reservoir for storing the at least one drug; and
    iii) an electric circuit comprising an electrode system of at least two electrodes, wherein the electrodes are disposed internally in the device such that the skin does not form part of the electric circuit and wherein the drug is actively transported from the reservoir in the direction of the skin when the electric circuit is energised;
  (b) providing a voltage potential across the electric circuit electrodes causing electrolytic transport of the at least one drug in a controlled manner within the device between the electrodes to provide controlled delivery of the at least one drug to the skin of the subject; and
  (c) delivering the at least one drug to the subject via controlled passive transdermal delivery.

41. A method for the controlled passive transdermal delivery of at least one drug to a subject, comprising the steps of:
  (a) attaching a transdermal device to the skin of the subject, wherein the transdermal device comprises:
    i) the at least one drug;
    ii) a reservoir for storing the at least one drug;
    iii) an electric circuit comprising an electrode system of at least two electrodes in which at least one of the electrodes is permeable to the at least one drug, wherein the electrodes are disposed internally in the device such that the skin does not form part of the electric circuit and wherein the drug is actively transported from the reservoir in the direction of the skin and through the at least one electrode permeable to the at least one drug when the electric circuit is energised;
    iv) a transit chamber adapted for contact with the skin, wherein the electrode permeable to the at least one drug is disposed between the reservoir for the drug and the transit chamber;
  (b) providing a voltage potential across the electric circuit electrodes causing the electrolytic transport of the at least one drug in a controlled manner within the device between the electrodes and from the reservoir through the electrode permeable to the at least one drug to the transit chamber to allow for the controlled delivery of the at least one drug to the skin of the subject from the transit chamber; and
  (c) delivering the at least one drug to the subject via controlled passive transdermal delivery.

* * * * *